United States Patent

Wang

[11] Patent Number: 6,021,353
[45] Date of Patent: Feb. 1, 2000

[54] ELECTRONIC MASSAGING DEVICE

[76] Inventor: Ching-Chuan Wang, 6F-3, No.213, Fu Ho Rd., Yung-Ho City, Taipei, Taiwan

[21] Appl. No.: 08/941,727
[22] Filed: Oct. 1, 1997
[51] Int. Cl.[7] .................................................... A61N 1/36
[52] U.S. Cl. .............................................................. 607/72
[58] Field of Search ................................ 607/59, 70, 72, 607/152

[56] References Cited

U.S. PATENT DOCUMENTS

| | | | |
|---|---|---|---|
| 4,690,145 | 9/1987 | King-Smith et al. | 607/72 |
| 4,693,254 | 9/1987 | Mickiewicz et al. | 607/59 |
| 5,048,523 | 9/1991 | Yamasawa et al. | 607/72 |
| 5,117,826 | 6/1992 | Bartelt et al. | 607/59 |
| 5,423,874 | 6/1995 | D'Alerta | 607/72 |

Primary Examiner—William E. Kamm
Attorney, Agent, or Firm—Bacon & Thomas

[57] ABSTRACT

An electronic massaging device includes a housing, a massaging portion, and a controlling circuit board. The housing includes a displaying portion and a keys portion. A controlling circuit board is disposed within the housing. The signal output from the keys portion can be transmitted to the controlling circuit board and is further converted into a pulse output. The massaging portion includes a pair of massaging media, a pair of conductive wires, and a connector which is electrically connected to the controlling circuit board. By this arrangement, the pulse output from the controlling circuit board can stimulate a muscle such that the muscle can be contracted to get the massaging effect.

5 Claims, 5 Drawing Sheets

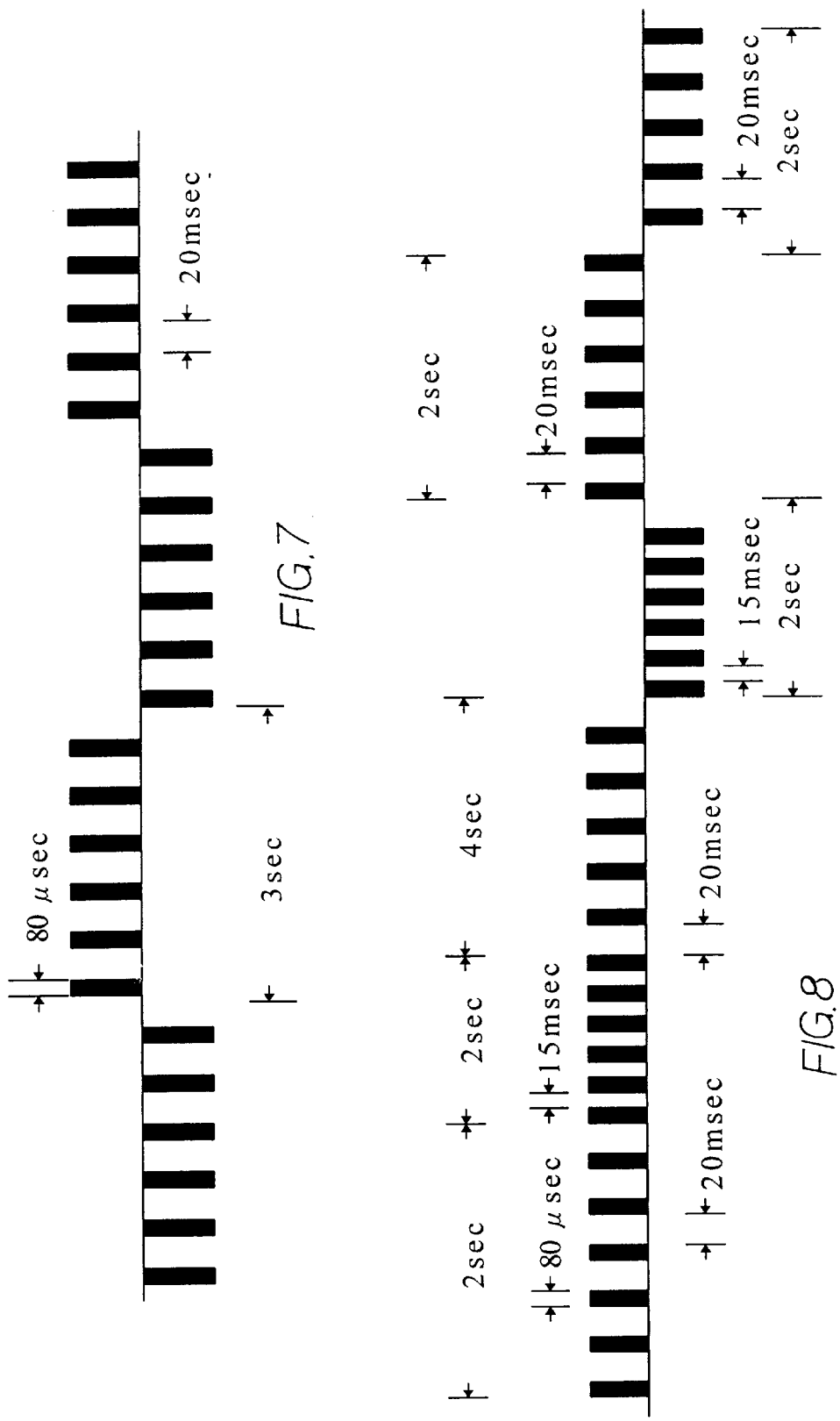

ELECTRONIC MASSAGING DEVICE

FIELD OF THE INVENTION

The present invention relates to a massaging device, and more particularly, to a messaging device in which the current resulting from surging voltage can be converted into a pulse output. The muscle can be suitably stimulated by the pulse output and experiences a contraction thereof. As a result, the muscle can be suitably massaged.

DESCRIPTION OF PRIOR ART

Massaging is an effective way to relieve muscle strain and increase blood circulation. The conventional massage applies pressure directly to the muscle and this can be done by oneself or others. However, this massaging is preferably done by someone skilled in the art in order to avoid an injury resulted from improper massaging. If the customer cannot find a massaging master, he/she may only conduct a massage by himself/herself. However, some parts of the body are inaccessible.

In order to have every part of body be massaged, an electrical massaging chair has been introduced. By providing such a massaging chair, some inaccessible parts of the body can be massaged. However, the existing massaging chair can only conduct a massage to certain parts of the body, i.e. the back or waist area. It cannot apply a massage to every part. Besides, the massaging chair is bulky and expensive. Furthermore, it is not portable and is not affordable for all families.

SUMMARY OF THE INVENTION

It is the objective of this invention to provide an electrical massaging device which is suitable for everyone.

It is the objective of this invention to provide an electrical massaging device with which a pulse is generated to stimulate the muscle to contract.

It is still the objective of this invention to provide an electronic massaging device which features a compact and portable configuration, and which device may apply a massage to any part of the body.

The electronic massaging device generally comprises a housing, a massaging portion, a controlling circuit board, and a displaying portion.

The housing has a displaying portion and a keys portion. The displaying portion is used to display the massaging condition and the keys portion can be used to supply an input to the controlling circuit board. A receiving space is defined by an upper and lower halves and the controlling circuit board is mounted therein.

The massaging portion includes a pair of massaging media, a pair of conductive wires and a connector. The massaging portion is electrically connected to the controlling circuit board and a pulse can be sent to the massaging portion for massaging.

The controlling circuit board includes a battery that supplies power to the board, an input circuit for receiving a plurality of different signals from the keys portion, a microprocessor having an input port, a controlling output port, and an output port, a logic circuit for receiving the controlling signal transmitted from the controlling output port and converting the controlling signal into different pulses, an output circuit for receiving a pulse from the logic circuit and transmitting the pulse to the massaging portion, and a displaying circuit for receiving the controlling output signal and the output signal from the controlling output port and the output port and display those signals.

The massaging portion can be electrically connected to the controlling circuit and the massaging media can be placed onto the portion to be massaged. Accordingly, the input signal from the keys portion can be converted into an output pulse by the controlling circuit board. The muscle may experience a contraction when the pulse is applied thereto.

BRIEF DESCRIPTION OF THE DRAWINGS

In order that the present invention may more readily be understood the following description is given, merely by way of example with reference to the accompanying drawings, in which:

FIG. 7 is a fourth pulse chart generated by the massaging device; and

FIG. 8 is a fifth pulse chart generated by the massaging device.

DETAILED DESCRIPTION OF PREFERRED EMBODIMENT

Figure 1:
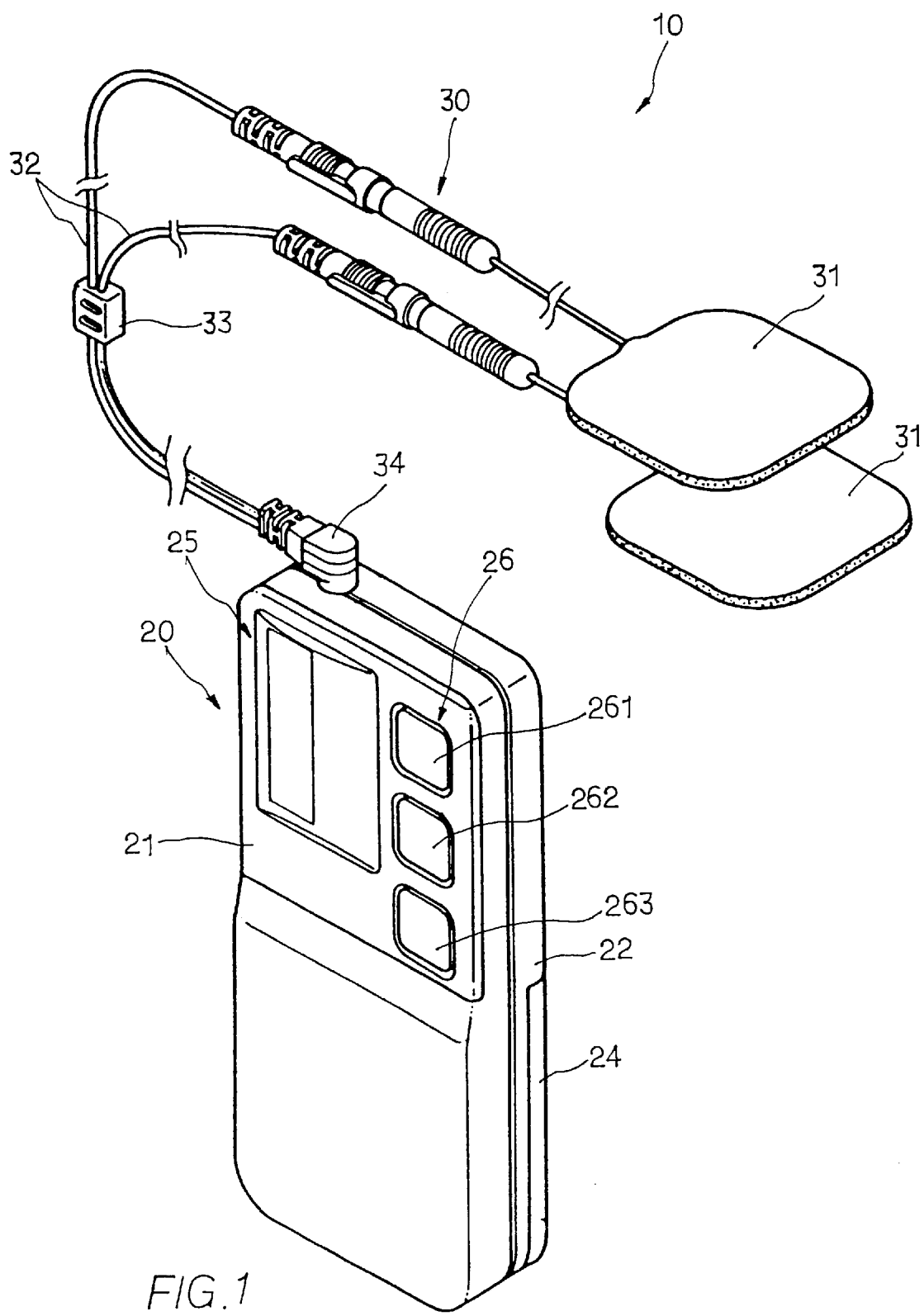
FIG. 1 is a perspective view of the massaging device made according to the present invention.
Figure 2:
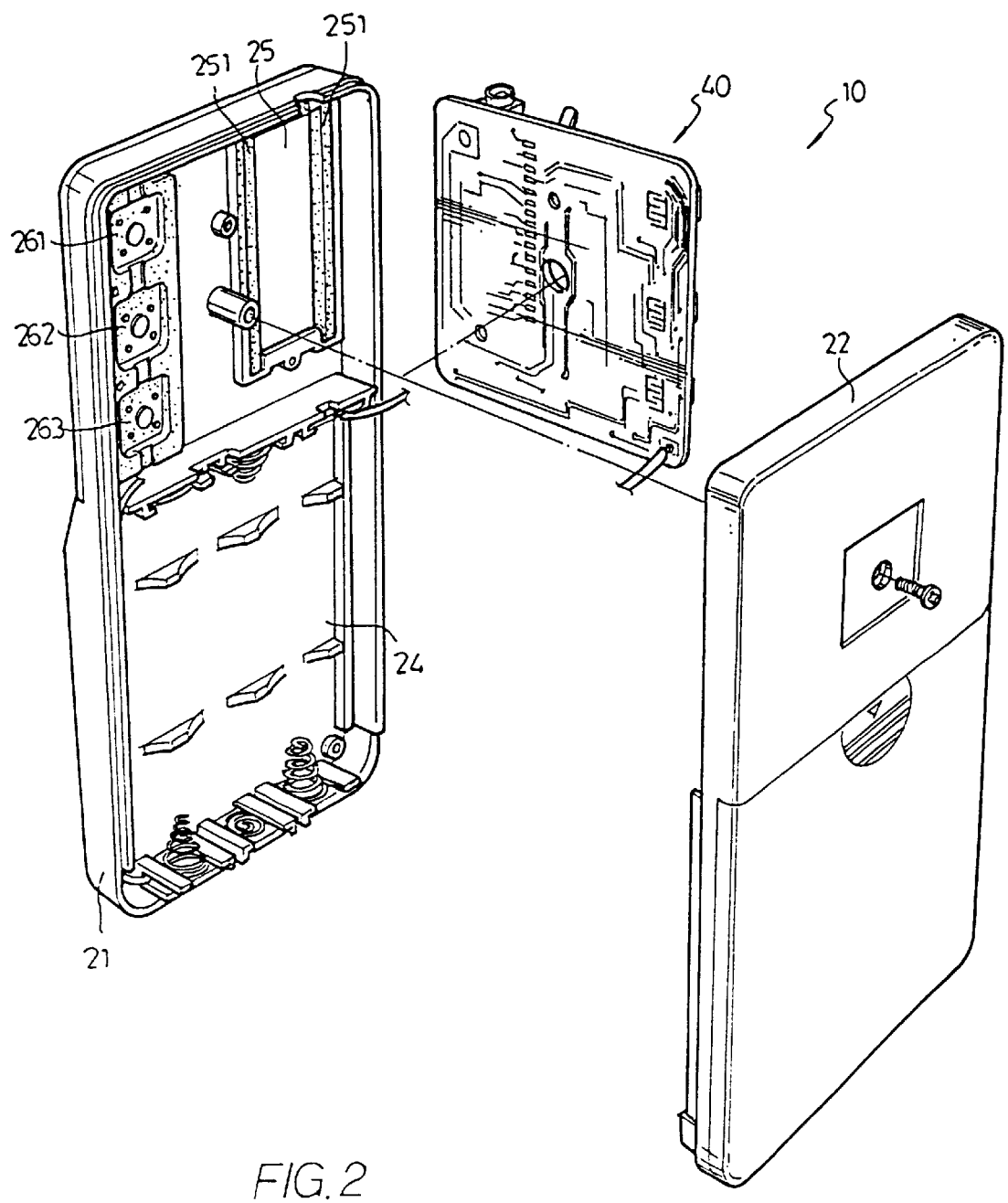
FIG. 2 is an exploded perspective view of the massaging device shown in FIG. 1.

Referring to FIGS. 1 and 2, the electronic massaging device 10 generally comprises a housing 20, a massaging portion 30, and a controlling circuit board 40.

The housing 20 is configured by an upper half 21 and a lower half 22 and a receiving space 24 is defined in the housing 20 when the upper and lower halves 21 and 22 are assembled. The upper half 21 is provided with a display portion 25 and a keys portion 26. In this embodiment, the displaying portion 25 is an LCD made from conductive rubber pad 251. The keys portion 26 is composed of an increasing key 261, a decreasing key 262, and a functional key 263. The electronic massaging device 10 is powered by a DC voltage and the receiving space 23 is provided with a compartment 24 for mounting a battery therein.

The massaging portion 30 generally includes a pair of massaging media 31, a pair of conducting wires 32, and a connector 34. The massaging media 31 can be made from a plastic sheet, a metal sheet and an adhesive which encloses one side of a conductive wire (not shown). The conductive wire is further connected to the conductive wires 32 and a connector 34 thereof, as clearly shown in FIGS. 1 and 2. In this embodiment, the conductive wires 32 are provided with a clip 33 which facilitates easy handling of the conducting wires 32.

Figure 3:
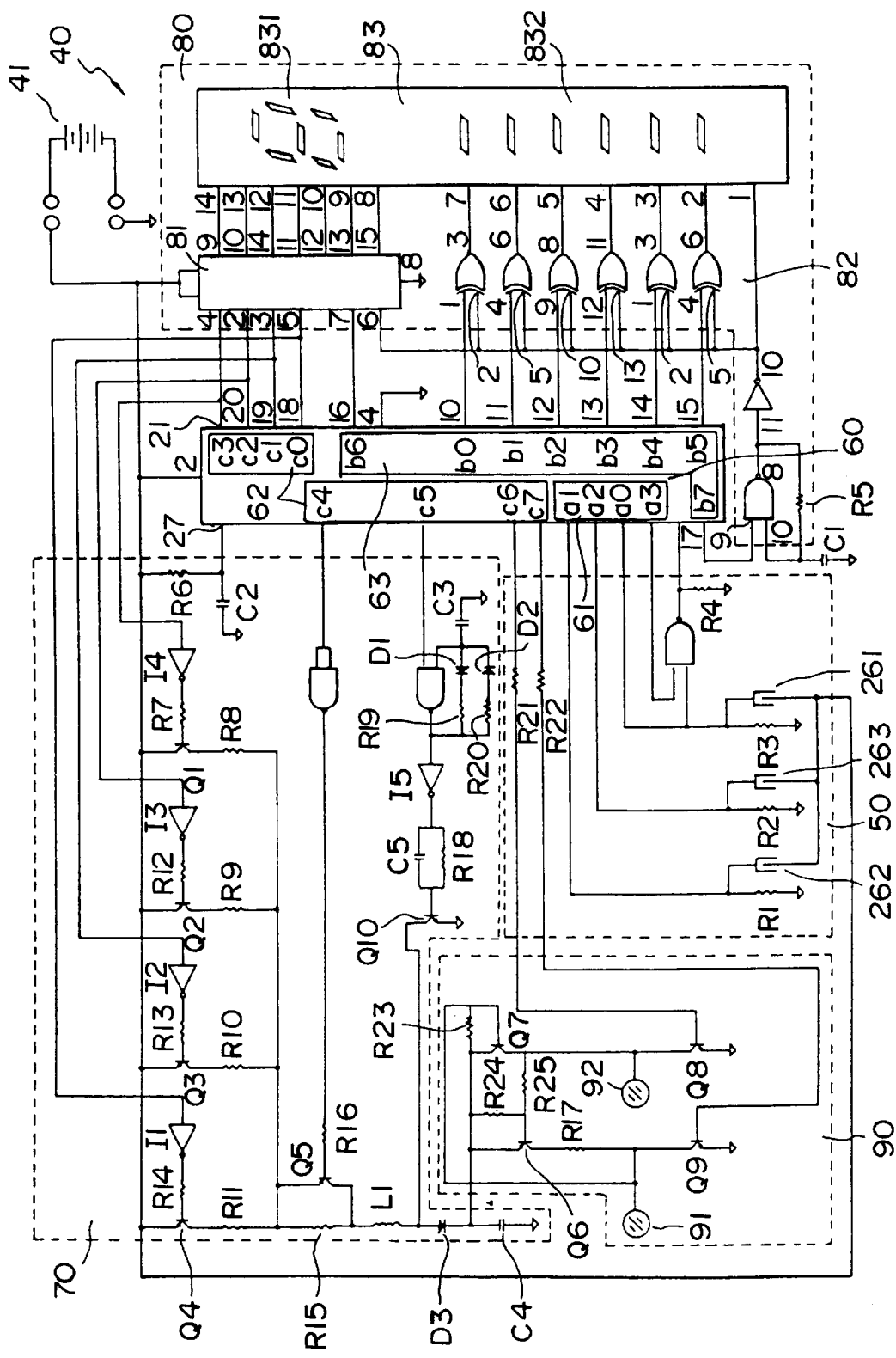
FIG. 3 is a circuitry incorporated in the massaging device.

Referring to FIG. 3, the controlling circuit board 40 generally comprises at least one battery 41, an input circuit 50, a microprocessor 60, a logic circuit 70, a displaying circuit 80, and an output circuit 90.

The controlling circuit board 40 is powered by the battery 41. Alternatively, the battery 41 can be also replaced by an AC/DC adaptor (not shown).

The input circuit 50 is electrically connected to the keys portion 26 and the input from the keys portion 26 can be used to control the input signal of the input circuit 50. The input circuit 50 can generate an increasing signal, decreasing signal or a functional signal corresponding to the actuation of the increasing key 261, the decreasing key 262, or the functional key 263. The signal output from the input circuit 50 is further sent to the microprocessor 60.

The microprocessor 60 is provided with an input port 61, a controlling output port 62, and an output port 63. The input port 61 is electrically connected to the input circuit 50 to receive the signal generated by the input circuit. After the received signal is further processed by the microprocessor 60, the signal is transmitted to the controlling output port 62 and to the output port 63 for generating a controlling signal and an output signal, respectively.

The logic circuit 70 can receive the controlling output signal from the controlling output port 62 and a plurality of different voltages and pulses can be generated thereby.

The output circuit 90 is provided with a first output terminal 91 and a second output terminal 92 for receiving a voltage and pulse, respectively, from the logic circuit 70. The received voltage and pulse are further transmitted to the connector 34 such that the voltage and pulse can be output by the massaging media 31. When these voltage and pulse are transmitted to the local area of the skin, an effective massaging is commenced.

The displaying circuit 80 includes a decoder 81, a plurality of logic gates 82, and a liquid crystal display (LCD) 83. The LCD 83 is further sub-divided into an intensity sector 831 and a function selecting sector 832. The intensity sector 831 and the function selecting sector 832 are electrically connected to the controlling output port 62 and the output port 63 respectively for converting the controlling output signal and the output signal into a graphic display. The controlling output signal is firstly decoded by the decoder 81 and then is displayed on the intensity sector 831 of the LCD 83. On the other hand, the output signal is firstly sent to the logic gate 82 and finally is displayed on the function selecting sector 832 of the LCD 83.

The operational styles and procedures will be described in more detail with respect to FIG. 3 as follows:

When the increasing key 261 of the keys portion 26 is depressed, the increasing signal generated therefrom is transmitted to the input port 61 of the input circuit 50. This increasing signal is further transmitted to the controlling output port 62 from the input port 61. Then this increasing controlling signal is transmitted to the logic circuit 70 and the displaying circuit 80 respectively from the controlling output port 62.

After the increasing signal is transmitted to the logic circuit 70, this signal is propagated by the invertor $I_1 \sim I_4$ such that the driving power of the microprocessor 60 can be increased. As a result, the surging output voltage from the logic circuit 70 can be increased. The more the increasing key 261 is depressed, the stronger is the surging output voltage output from the output circuit 90.

When the increasing signal is transmitted to the displaying circuit 80, the decoder will verify the intensity level of the increasing signal and the intensity level will be digitized and displayed on the LCD 83. By this arrangement, the user can be clearly advised of the intensity level.

Conversely, when the decreasing key 262 of the keys portion 26 is depressed, the more the decreasing key 262 is depressed, the surging output voltage output from the logic circuit 70 is reduced. In this preferred embodiment, when the surging output voltage is lower than a threshold, the power from the battery will be cut. Of course, the intensity level of the decreasing signal will also be displayed on the LCD 83.

On the other hand, when the functional key 263 is depressed, a different functional converting signal will be sent to the input port 61. In this embodiment, there are six different functional converting signals. The pulse output of those signal will be described in detail later. In addition, the different functional converting signals are further transmitted to the controlling output port 62 and the output port 63.

When the functional converting signal is output to the logic circuit 70 from the controlling output port 62, it is converted into a high frequency pulse cut signal which can be used to generate a surging output voltage. The surging output voltage is then transmitted to the output circuit 90, from which a high frequency pulse will be output.

On the other hand, the functional converting signal transmitted by the output port 63 is displayed on the LCD 83 through the logic gate 82. Accordingly, an instant high frequency output can be clearly shown on the LCD 83.

In this preferred embodiment, there are six different high frequency pulse output generated from the functional converting signal.

Figure 4:
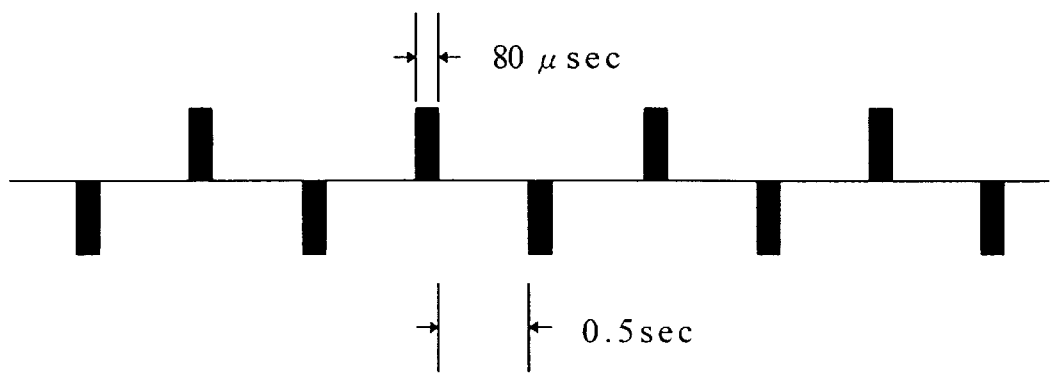
FIG. 4 is a first pulse chart generated by the massaging device.
Figure 5:
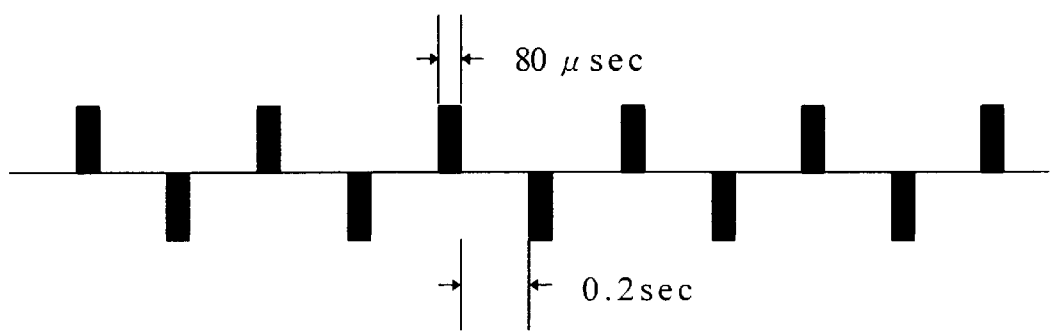
FIG. 5 is a second pulse chart generated by the massaging device.

As shown in FIG. 4, the first pulse output pattern begins with a positive pulse which lasts for 80 usec. Then after an interval of 0.5 sec, a negative pulse which lasts for 80 usec is then generated. These positive and negative pulses will be alternatively generated unless another pattern is selected. This massaging pattern simulates a hammering massage.

The second pulse output pattern is similar to the first pulse output pattern, but the interval between the positive and the negative pulse is decreased to 0.2 sec. In this case, the frequency of hammering massaging is increased. This massaging pattern will also be repetitively performed unless another massaging pattern is selected.

Figure 6:
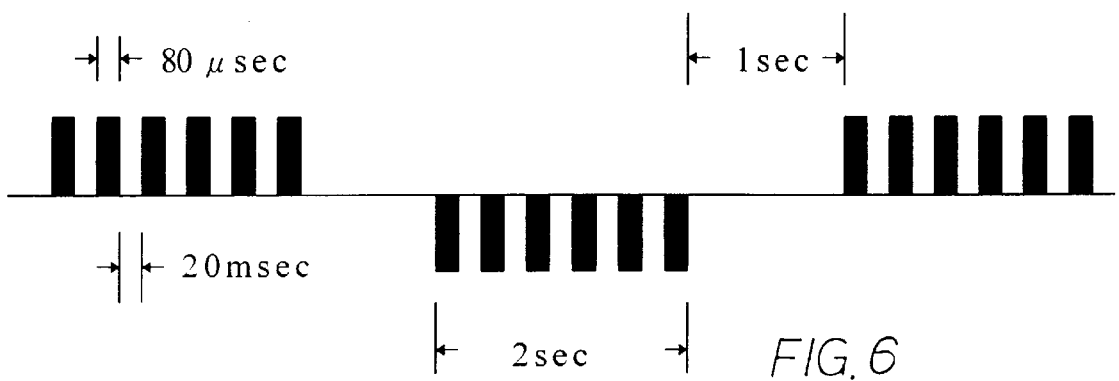
FIG. 6 is a third pulse chart generated by the massaging device.

FIG. 6 shows another type of massaging pattern. In this third pulse output pattern, a plurality of positive pulses are generated consecutively. The duration of each of the individual positive pulse lasts for 80 usec and the interval therebetween is about 20 msec. After a 1 sec period, a plurality of negative pulses are generated consecutively. The duration of each individual negative pulse lasts for 80 usec and the interval therebetween is also about 20 msec. The overall duration of the positive and negative pulse in a single cycle is 2 sec, i.e. a plurality of positive pulses or negative pulses are generated within a period of 2 seconds. This massaging pattern simulates a soft and tender massage. This massaging pattern will also be repetitively performed unless another massaging pattern is selected.

FIG. 7 discloses a fourth pulse output pattern and which is similar to the third pulse output pattern shown in FIG. 6. In this third pulse output pattern, a plurality of positive pulses are generated consecutively within a period of 3 seconds. The duration of each of the individual positive pulse lasts for 80 usec and the interval therebetween is about 20 msec. After a 20 msec period, a plurality of negative pulses are generated consecutively within another 3 seconds. The duration of each individual negative pulse lasts for 80 usec and the interval therebetween is also about 20 msec. This massaging pattern simulates an intensified massaging. This massaging pattern will also be repetitively performed unless another massaging pattern is selected.

FIG. 8 discloses a fifth pulse output pattern which is a composite massage that combines a plurality of pulse patterns. Within the first 2 seconds, a plurality of positive pulses which are generated for 80 usec with an interval between pulses of about 20 msec is also generated. When the second 2 seconds period, a plurality of positive pulses which last for 80 usec with an interval therebetween is also about 15 msec is also generated. Then in the third 4 seconds period, a plurality of positive pulses which last for 80 usec with an interval therebetween of about 20 msec is generated. Afterward, in the fourth 2 seconds period, a plurality of negative pulses which lasts for 80 usec with an interval therebetween of about 15 msec is generated. Then in the fifth 2 seconds period, a plurality of positive pulses which last for 80 usec with an interval therebetween of about 20 msec is generated. In the last 2 seconds period, a plurality of negative pulses which lasts for 80 usec with an interval therebetween of about 20 msec is generated. This composite massaging pattern simulates a push-and-roll massaging pattern. This massaging pattern will also be repetitively performed unless another massaging pattern is selected.

The six pulse output style (not shown) is a composite pulses output pattern in which the five massaging patterns have been combined. Each of the pulse patterns lasts for 20 seconds and this will be repetitively performed unless another massaging pattern is selected.

The microprocessor 60 is provided with a built-in timer (not shown) and which is used to count the massaging time of the pulses output. Also, the massaging device will be shut off after 15 minutes from the switching on of the massaging device.

From the forgoing description, it can be readily appreciated that the rescuing helmet features a simple, compact configuration which can be readily manufactured with lowered cost. While particular embodiment of the present invention has been illustrated and described, it would be obvious to those skilled in the art that various other changes and modifications can be made without departing from the spirit and scope of the invention. It is therefore intended to cover in the appended claims all such changes and modifications that are within the scope of the present invention.

I claim:
1. An electronic massaging device, comprising:
   a housing including an upper half and a lower half, a receiving space being defined in said housing when the upper and lower halves are assembled, the upper half being provided with a displaying portion and a keys portion including an increasing key, a decreasing key, and a function selection key;
   a massaging portion including a pair of massaging media, a pair of conducting wires, and a connector; and
   a controlling circuit board comprising:
      at least one battery arranged to provide power required by the controlling circuit board;
      an input circuit electrically connected to said battery and to said keys portion, said input circuit being arranged to output, depending on which of the increasing, decreasing, and function selection keys is pressed, an increasing signal, a decreasing signal, and a function selection signal;
      a logic circuit arranged to generate pulses;
      a microprocessor having an input port, a controlling output port, and an output port, said input port being electrically connected to said input circuit to receive said respective increasing, decreasing, and function selection signals, said controlling output port being connected to said logic circuit, and said output port being connected to a display circuit,
      wherein said microprocessor is arranged to generate, and supply to said controlling output port, a controlling signal which controls a pattern and amplitude of said pulses generated by the logic circuit in response to said increasing, decreasing, and function selection signals, as follows:
         (i) said controlling signal causes said logic circuit to output a different predetermined pattern of pulses each time said function selection signal is received,
         (ii) said controlling signal causes an amplitude of said pulses to be increased in response to receipt of said increasing signal; and
         (iii) said controlling signal causes an amplitude of said pulses to be decreased in response to receipt of said decreasing signal,
      wherein said microprocessor also generates an output signal which is representative of a selected pattern of pulses and which is supplied to a display circuit through said output port, and
      wherein said display circuit including a decoder connected to said controlling output port of said microprocessor, a plurality of logic gates connected to output port of said microprocessor, and a liquid crystal display (LCD) connected to said decoder and to said plurality of logic gates, said LCD being further sub-divided into an intensity sector and a function selecting sector, said controlling output signal being firstly decoded by said decoder and then displayed on said intensity sector of said LCD, and said output signal being sent to said logic gates and displayed on said function selecting sector of said LCD; and
      an output circuit connected to said logic circuit and arranged to supply said pulses to said pair of wires, and thereby to said massaging medium,
   wherein the pulse output from said output circuit via said pair of wires to said massaging medium stimulates a muscle thereunder such that the muscle is contracted and a massaging effect is attained.

2. An electronic massaging device as recited in claim 1, wherein an compartment for said battery is defined within said receiving space.

3. An electronic massaging device as recited in claim 1, wherein said display portion is a liquid crystal display.

4. An electronic massaging device as recited in claim 1, wherein said microprocessor is provided with a built-in timer arranged to shut off the massaging device a predetermined time after the massaging device is switched on.

5. An electronic massaging device as recited in claim 1, further comprising an A/C adaptor arranged to supply power to said controlling circuit board.

* * * * *